US012268810B2

United States Patent
Montgomery et al.

(10) Patent No.: US 12,268,810 B2
(45) Date of Patent: Apr. 8, 2025

(54) EMERGENCY INCISION AND DILATION APPARATUS AND METHOD

(71) Applicant: Wolf Technical Services, Inc., Fishers, IN (US)

(72) Inventors: Melissa Montgomery, Alexandria, VA (US); Aaron James Tolly, Fishers, IN (US); Jarrett Waters, Camby, IN (US)

(73) Assignee: Wolf Technical Services, Inc., Fishers, IN (US)

( * ) Notice: Subject to any disclaimer, the term of this patent is extended or adjusted under 35 U.S.C. 154(b) by 819 days.

(21) Appl. No.: 17/610,645

(22) PCT Filed: Jun. 2, 2020

(86) PCT No.: PCT/US2020/035763
§ 371 (c)(1),
(2) Date: Nov. 11, 2021

(87) PCT Pub. No.: WO2020/247396
PCT Pub. Date: Dec. 10, 2020

(65) Prior Publication Data
US 2022/0211959 A1    Jul. 7, 2022

Related U.S. Application Data

(60) Provisional application No. 62/856,126, filed on Jun. 2, 2019.

(51) Int. Cl.
*A61M 16/00* (2006.01)
*A61B 17/3211* (2006.01)
(Continued)

(52) U.S. Cl.
CPC ..... *A61M 16/0003* (2014.02); *A61B 17/3211* (2013.01); *A61M 29/02* (2013.01);
(Continued)

(58) Field of Classification Search
CPC .............. A61M 16/0003; A61M 29/02; A61M 2029/025; A61M 16/0465;
(Continued)

(56) References Cited

U.S. PATENT DOCUMENTS 3,817,250 A    6/1974  Weiss et al.
3,991,765 A  * 11/1976  Cohen ............... A61M 16/0472
                                               128/207.29

(Continued)

OTHER PUBLICATIONS

International Search Report corresponding to International Patent Application No. PCT/US2020/035763, dated Sep. 10, 2020 (2 pages).

*Primary Examiner* — Timothy A Stanis
*Assistant Examiner* — Tina Zhang
(74) *Attorney, Agent, or Firm* — Maginot, Moore & Beck LLP (57) ABSTRACT

An incision and dilation apparatus performs an incision in and dilates select tissue of a mammal. The apparatus includes a blade member, a dilator, and a frame. The blade member includes a blade having a cutting edge. The dilator is configured to dilate the select tissue. The frame includes a blade guide, and is adapted to position the blade guide over the select tissue. The blade guide retains the blade member in first and second perpendicular directions and allows substantially linear movement of the blade member in a third direction. The frame also supports the dilator and allows movement of the dilator in the third direction. The dilator includes a second blade guide that retains the blade member in first and second perpendicular directions and allow substantially linear movement of the blade member relative to the dilator in a third direction.

20 Claims, 9 Drawing Sheets

(51) Int. Cl.
*A61M 29/02* (2006.01)
*A61B 17/32* (2006.01)

(52) U.S. Cl.
CPC ............ *A61B 2017/320052* (2013.01); *A61M 2029/025* (2013.01)

(58) Field of Classification Search
CPC .... A61M 2025/09116; A61M 16/0434; A61M 16/0484; A61M 16/0488; A61M 16/04; A61M 16/0472; A61B 2017/0046; A61B 17/0483; A61B 17/2841; A61B 17/2909; A61B 2017/2918; A61B 1/00066; A61B 1/00121; A61B 2017/320052; A61B 17/32; A61B 17/3209; A61B 17/3211; A61F 2/9517
USPC .................................................... 128/207.29
See application file for complete search history.

(56) References Cited

U.S. PATENT DOCUMENTS

| | | | |
|---|---|---|---|
| 4,331,138 A * | 5/1982 | Jessen | ............... A61M 16/0472 |
| | | | 128/207.29 |
| 5,972,014 A | 10/1999 | Nevins | |
| 8,215,309 B2 | 7/2012 | Single, Jr. | |
| 2014/0148837 A1 | 5/2014 | Levitan | |
| 2018/0008792 A1 | 1/2018 | Harris et al. | |

* cited by examiner

EMERGENCY INCISION AND DILATION APPARATUS AND METHOD

This application claims the benefit of U.S. Provisional Patent Application Ser. No. 62/856,126, filed Jun. 2, 2019

STATEMENT REGARDING FEDERALLY SPONSORED RESEARCH OR DEVELOPMENT

This invention was made under a contract with the United States government Department of Defense under DOD Contract No. W81XWH-14-C-0012. The government has certain rights in the invention.

FIELD OF THE INVENTION

The present invention relates generally to medical emergency devices, and particularly, to devices that make incisions into and dilate tissue.

DESCRIPTION OF THE RELATED ART

In some cases, medical emergencies arise in which an incision and dilation of tissue must be performed quickly, such as in a cricothyrotomy. A cricothyrotomy is a medical procedure that involves creating an incision in the cricothyroid membrane. The cricothyroid membrane is a membrane in the neck proximate to what is commonly referred to as the Adam's Apple. One purpose of a cricothyrotomy is to create an emergency pathway to the lungs of a patient for respiration, when the normal pathway through the nose and/or mouth is compromised. After the incision in the cricothyroid membrane is completed, a tube is place through the incision site and into the patient's airway. The lungs of the patient may then exchange gas (inhale and exhale) through the tube.

Cricothyrotomies are of particular use when time is critical and access to immediate hospital care is not available. Such situations can include, but are not limited to, combat and disaster site situations. Cricothyrotomy kits contain devices that assist in the cricothyrotomy procedure, and are often provided to first responders and field medical personnel.

One popular prior art cricothyrotomy kit contains only the basic tools needed to perform an emergency cricothyrotomy. Such kits contain a scalpel, a hook device, and a tube. The scalpel is used to cut the cricothyroid membrane, and the hook device is used to spread the spread the incision site to allow insertion of the tube. While this is technically sufficient, the included tools provide scant protection against many of the common errors that are encountered while performing this procedure on the battlefield, such as misidentification of anatomical landmarks, posterior tracheal perforation, and mediolateral misalignment. In addition, the components are loosely packaged in the kit, relying on the user to recall proper procedural order and equipment usage. This can easily become confusing for the user during a high-stress scenario.

Another kit, called the NuTrake is a kit that uses a split-needle design that expands the opening after puncture. This allows for one of three tracheal tubes to be inserted into the surgical airway. While the split needle design eliminates some of the confusion and stress associated with use of the hook device for spreading the opening, it still shares several shortcomings of the basic kit. For example, this device also relies on the manual location of the cricothyroid membrane by the medic or physician.

Other devices have attempted to address some of the issues of the basic cricothyrotomy kits, but have their own shortcomings. For example, one device punctures both the skin and the membrane using a sharp metal trocar/obturator that is nested in a plastic cannula. Upon successful puncture, a safety stopper is removed, and the trocar/obturator is removed, leaving behind the plastic cannula. In theory this approach seems to be very beneficial, as it can reduce procedure time compared to traditional approaches. However, in mid-procedure, the only safety stop (which limits the possibility of posterior tracheal perforation), is removed. At this time, the device is not yet fully inserted. The next step requires that the user carefully advance the plastic cannula forward while simultaneously retracting the sharp metal trocar/obturator. This technique may be sufficient for an emergency room or other hospital situation where the patient is secured. However, this method is risky in a battlefield scenario when the possibility of patient movement relative to the device during insertion is highly probable. In addition to this flaw in the device safety, the device also requires that the user angle the device during insertion to help prevent posterior tracheal wall perforation. Should the user omit this step or perform it incorrectly, the patient is at risk for additional injury.

Another device is that disclosed is United States Patent Publication No. 2018/0008792, which includes a blade and a dilation tool that can be positioned and guided by a special frame that aligns to the sternal notch. While such a device represents an improvement over the prior art, the blade portion is exposed and can inadvertently move in different ways, which can lead to the requirement of additional training and safety procedures.

SUMMARY OF THE INVENTION

At least some embodiments address one or more drawbacks of the prior art by providing an incision and dilation arrangement that may be used, for example, in a cricothyrotomy kit, and which features additional safety structures.

A first embodiment is an incision and dilation apparatus for performing an incision in and dilating select tissue of a mammal. The apparatus includes a blade member, a dilator, and a frame. The blade member includes a blade having a cutting edge. The dilator is configured to dilate the select tissue. The frame includes a blade guide, and is adapted to position the blade guide over the select tissue. The blade guide retains the blade member in first and second perpendicular directions and allows substantially linear movement of the blade member in a third direction. The frame also supports the dilator and allows movement of the dilator in the third direction. The dilator includes a second blade guide that retains the blade member in first and second perpendicular directions and allow substantially linear movement of the blade member relative to the dilator in a third direction.

The second blade guide on the dilator provides a second retention mechanism that helps ensure predictable movement of the blade with respect to the dilator, which is typically part of an incision and dilation procedure.

A second embodiment is also an incision and dilation apparatus for performing an incision in and dilating select tissue of a mammal. The apparatus of the second embodiment includes a blame member, a dilator, a frame and a removable clip. The blade member includes a blade having a cutting edge. The dilator is configured to dilate the select tissue. The frame includes a blade guide, and is adapted to position the blade guide over the select tissue. The blade guide retains the blade member in first and second perpendicular directions and allows substantially linear movement of the blade member in a third direction. The frame also supports the dilator and allows movement of the dilator in the third direction. The removable clip extends over and engages a portion the dilator and the blade member to restrict movement of at least the blade member.

The above-described features and advantages, as well as others, will become more readily apparent to those of ordinary skill in the art by reference to the following detailed description and accompanying drawings.

DETAILED DESCRIPTION

Figure 2:
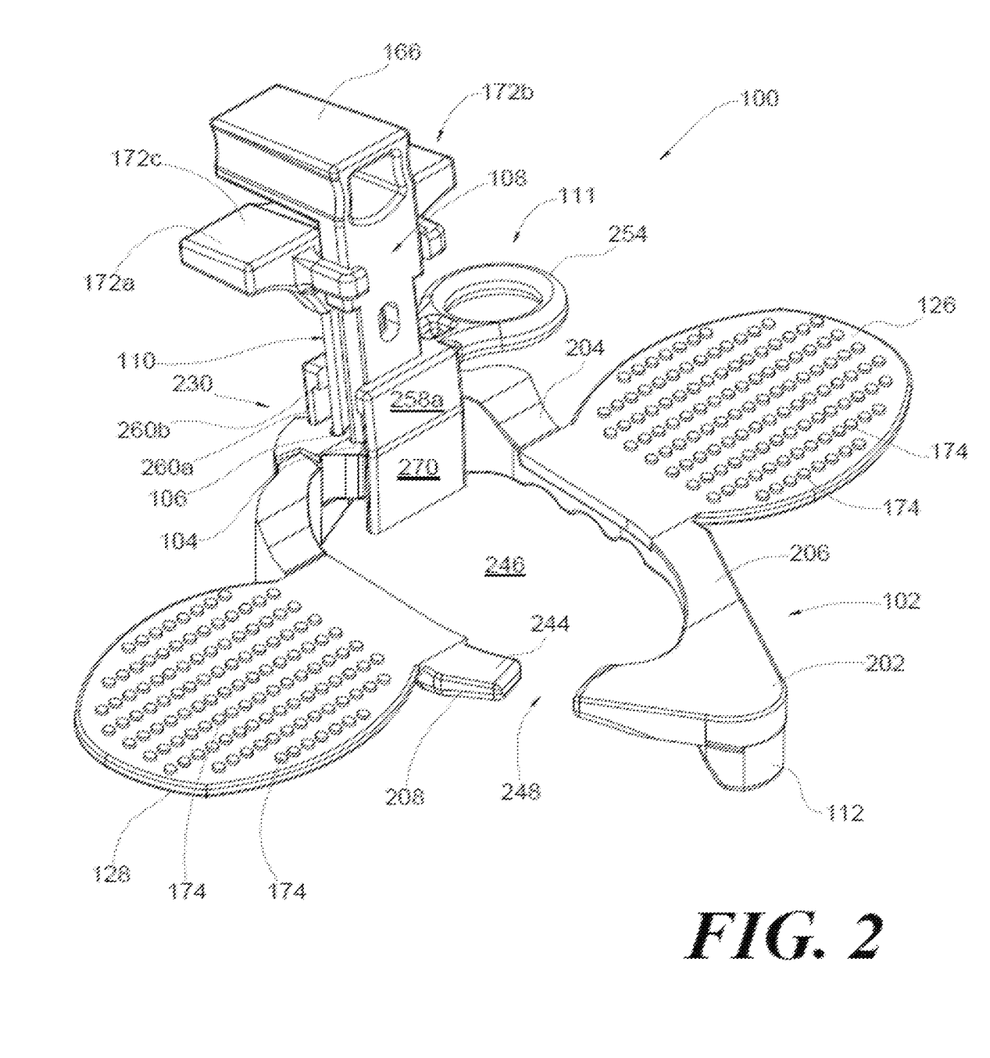
FIG. 2 shows a perspective view of a cricothyrotomy apparatus according to an exemplary embodiment of the invention.
Figure 3:
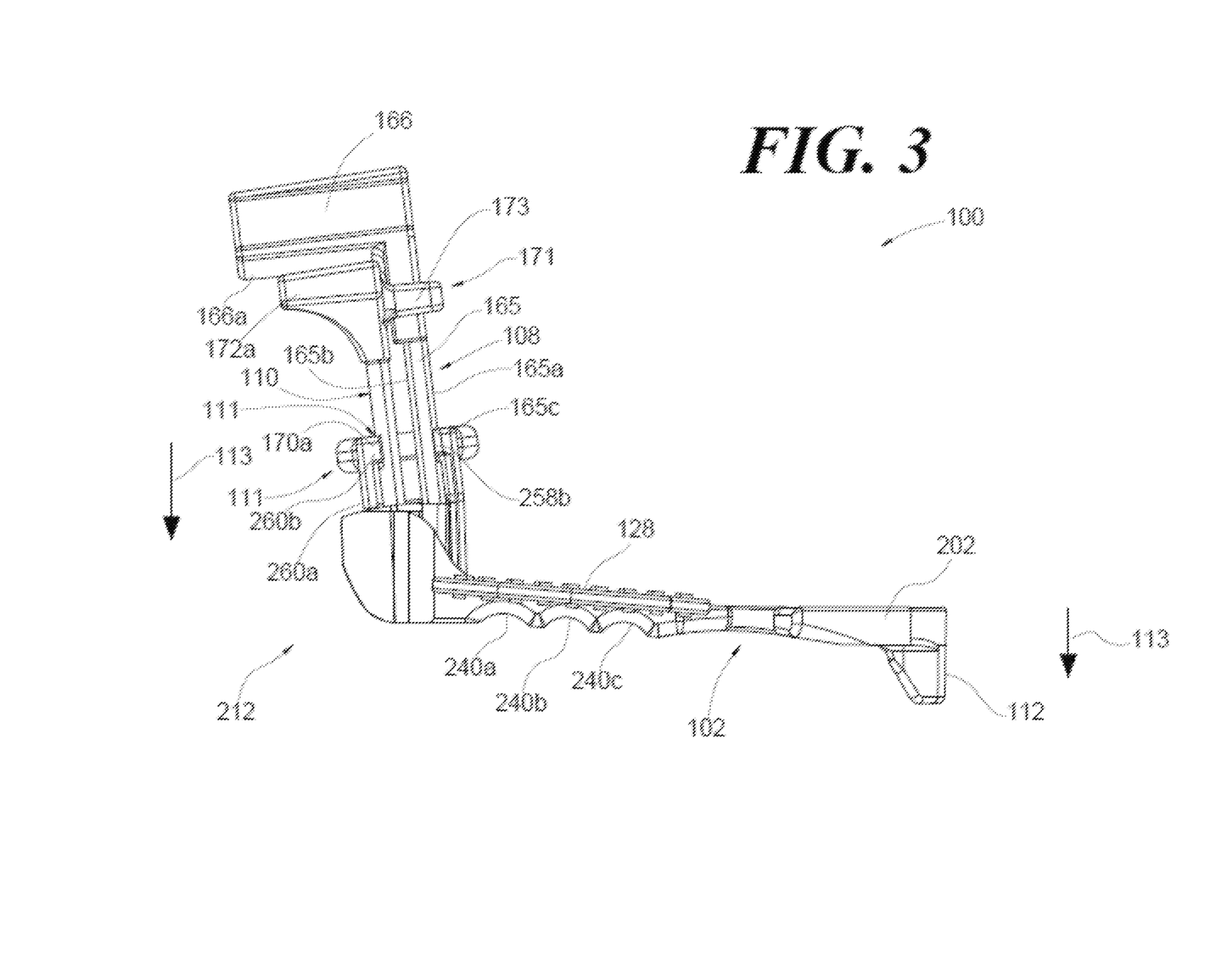
FIG. 3 shows a side plan view of the cricothyrotomy apparatus of FIG. 2.
Figure 4:
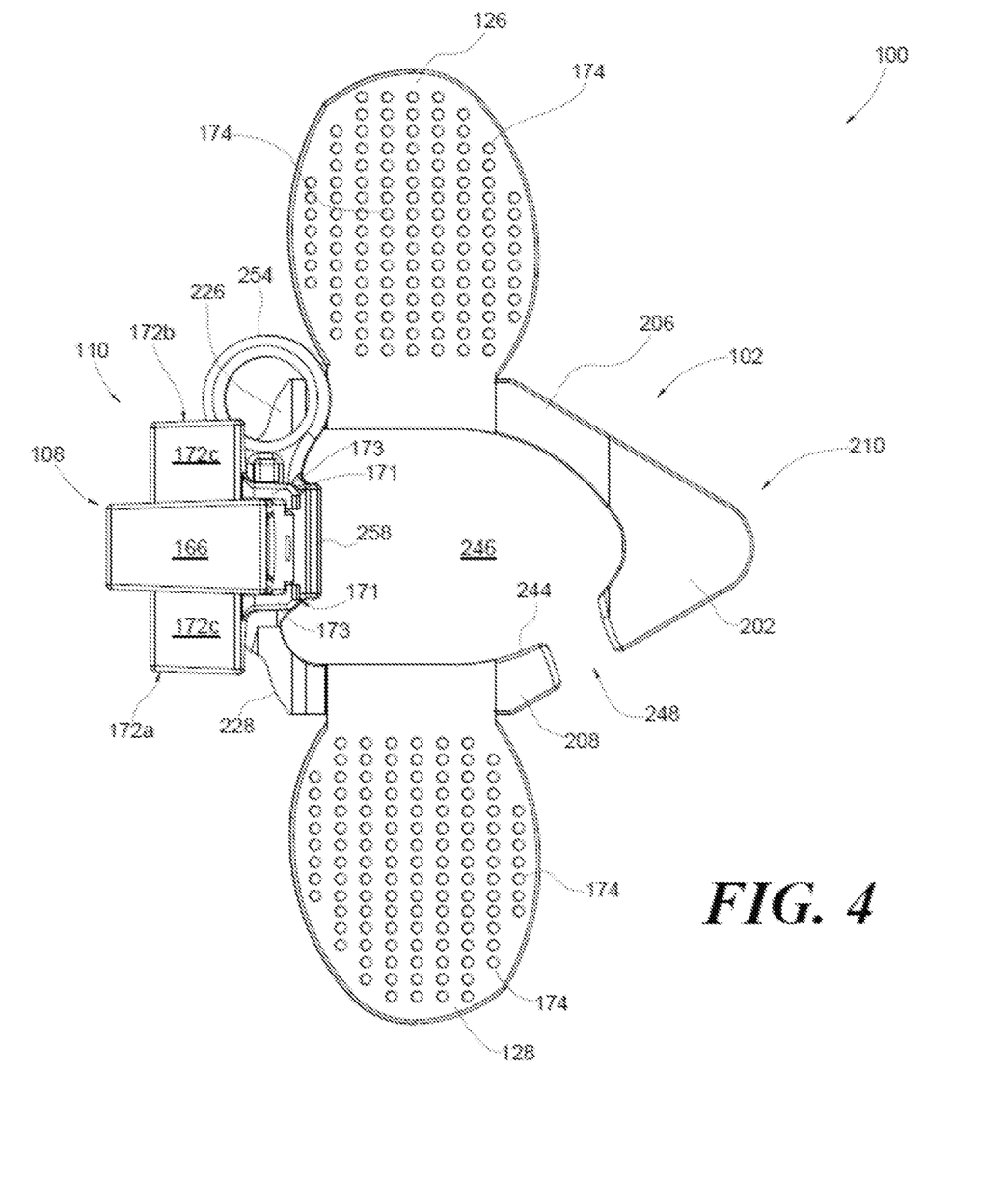
FIG. 4 shows a top plan view of the cricothyrotomy apparatus of FIG. 2.

FIG. 2 shows a perspective view of an incision and dilation apparatus 100 according to an exemplary embodiment of the invention. FIG. 3 shows a side plan view of the apparatus 100, and FIG. 4 shows a top plan view of the apparatus 100. The incision and dilation apparatus 100 in the exemplary embodiment described herein is intended for use in a cricothyrotomy, and thus has features specific to performing incision and dilation of the cricothyroid membrane. However, it will be appreciated that the incision and dilation apparatus described herein may readily be adapted to perform incision and dilation of other tissue of a human or mammal.

With contemporaneous reference to FIGS. 2-4, the apparatus 100 includes a frame 102, a blade member 108, a dilator 110, a clip member 111, a sternal notch alignment piece 112, and first and second wings 126, 128. The frame 102 further includes a blade guide 104 and a dilator guide 106.

The sternal notch alignment piece 112 is a protuberance, for example, a knob or boss, extending in a downward direction 113 from the frame. In relation to use of the device, the downward direction 113 generally means toward the tissue to be dilated. In this embodiment, the downward direction 113 is the anterior-posterior direction. The protuberance 112 is located at a distance from the blade guide 104 that corresponds to the distance between a sternal notch of an adult human and a cricothyroid membrane of the adult human. The protuberance 112 is sized and configured to be at least partly received and seated by a sternal notch of an adult human, over the skin. It will be appreciated that one or more alternative embodiments can be used with children, having a reduced distance from the protuberance 112 to the blade guide 104.

Figure 1:
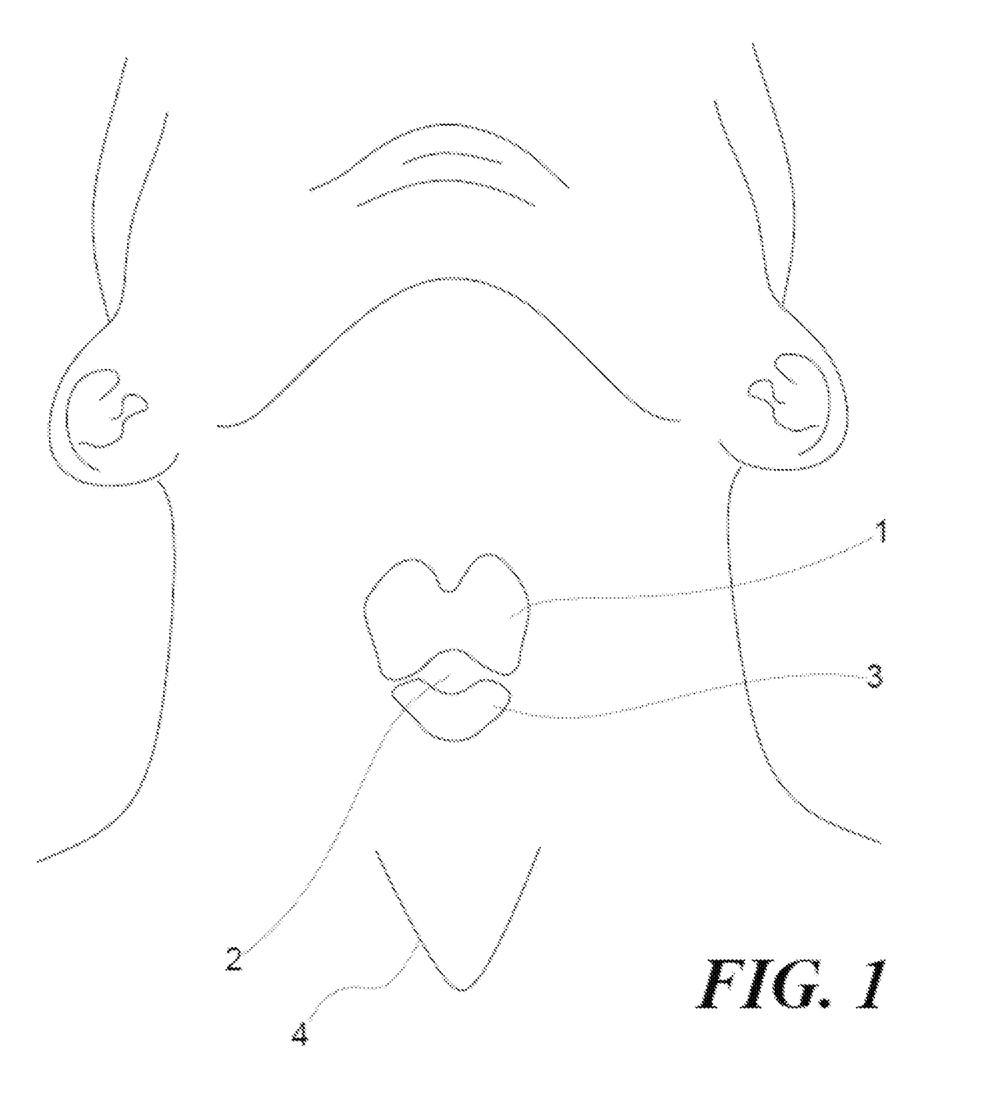
FIG. 1 shows a diagram of a neck of a human patient illustrating the location of the cricothyroid membrane.

Referring to FIG. 1, the suprasternal notch 4 of a human is located at the superior end of the sternum, and can be easily identified by touch at the base on the anterior portion of the neck. The cricothyroid membrane 2 is located, in adult humans, at a substantially uniform distance from the suprasternal notch 4, approximately 70 mm, and is between the thyroid cartilage 1 and the cricoid cartilage 3. Referring to FIGS. 1 to 4, the protuberance 112 and the blade guide 104 are configured such that when the protuberance 112 is seated within at least a portion of the sternal notch 4, the blade guide 104 is aligned over the cricothyroid membrane 2.

As used herein all references to relative positions and directions, namely, anterior, posterior, superior, inferior, medial and lateral, shall be with respect to the proper placement of the apparatus 100 on a human neck, such that the protuberance 112 is seated at least partially within the sternal notch 4, the blade guide 104 is disposed over the cricothyroid membrane 2, and the frame 102 extends long the neck portions in between the sternal notch 4 and the cricothyroid membrane 2.

Figure 8:
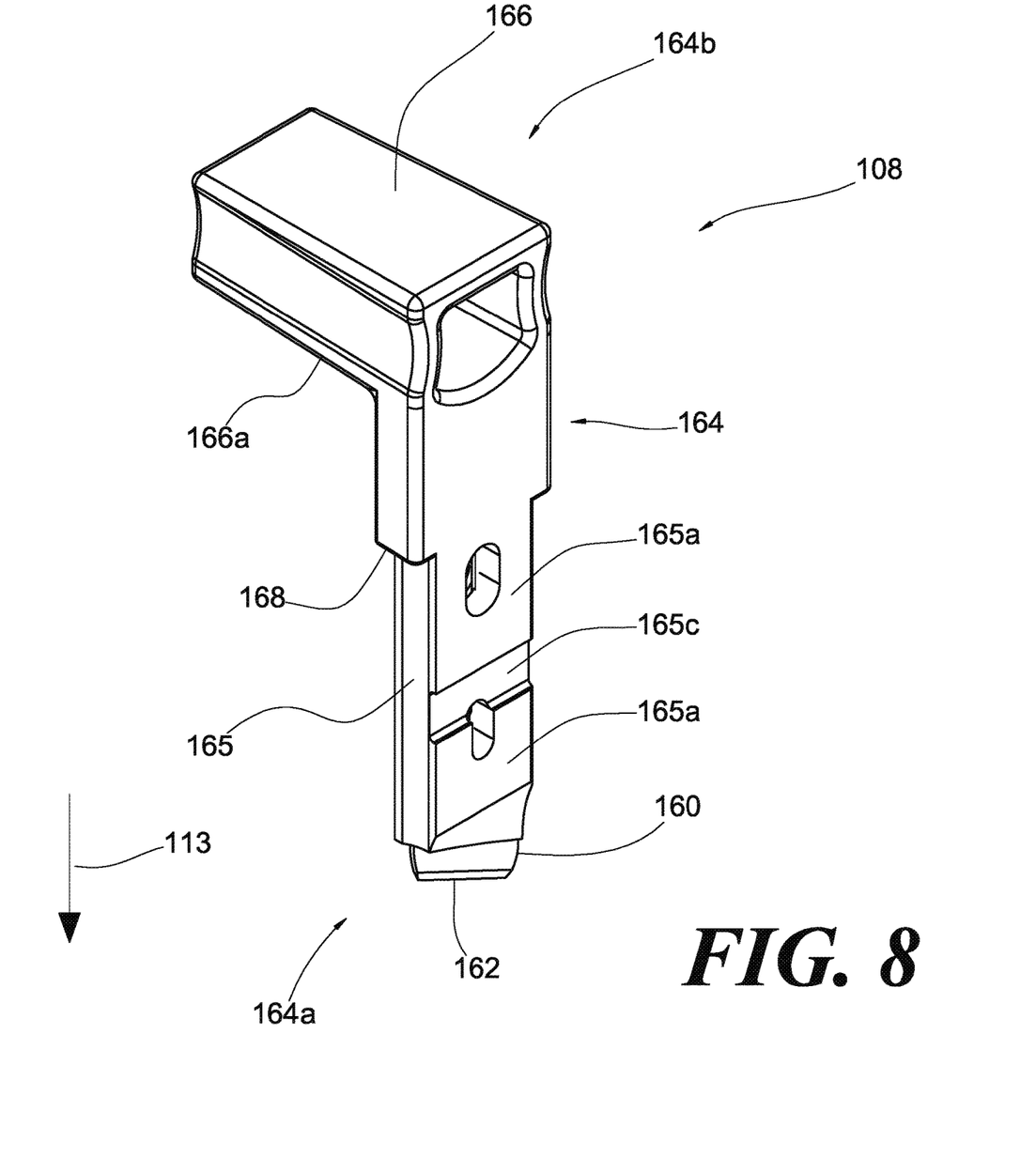
FIG. 8 shows a perspective view of an exemplary embodiment of the blade member of the cricothyrotomy apparatus of FIG. 2.

In this embodiment, the blade member 108 is slidably disposed within the blade guide 104. FIG. 8 shows a plan view of an exemplary blade member 108. The blade member 108 includes a blade 160 having a cutting edge 162, and a blade frame 164. The blade frame 164 has a first end 164a, a second end 164b, a sliding bar 165, a button 166, and a shoulder 168. The blade 160 is supported by the blade frame 164 and extends from the first end 164a of the blade frame such that a blade edge 162 is external to the blade frame 164.

As shown in FIG. 8, the sliding bar 165 extends in the downward (i.e. up-down) direction, and may suitably be formed of molded plastic material. The sliding bar 165 has a generally uniform width, and furthermore has a generally flat front surface 165a and generally flat back surface 165b, not shown in FIG. 8 but see FIG. 3. Most of the shaft of the blade 160, not shown is disposed within and rigidly supported by the sliding bar 165. Although the front surface 165a is generally flat, the front surface 165a includes an indentation 165c configured to receive a clip 250 of the clip member 111 (see also FIG. 9), as will be discussed below. In this embodiment, the indentation 165c is a linear channel defined in the medial-lateral direction. However, in other embodiments, the indentation 165a may be a round depression or other type of indentation that can seat with portions of a corresponding embodiment of the clip 250.

The button 166 forms a handle/manipulation mechanism and is disposed at the second end 164b of the blade frame 164. The button 166 extends horizontally, such that the button 166 and the sliding bar 165 are substantially perpendicular to each other. As shown in FIGS. 2 and 3, the button 166 extends horizontally and over a top surface 172c of the dilator 110, such that a bottom surface 166a of the button 166 can engage the top surface of the dilator 110 (see also FIG. 3). The button 166 in this embodiment is a hollow bar having a width sufficient to facilitate structural integrity and digital manipulation. The bottom surface 166a of the button 166 is curved.

The blade 160 may suitably be a commercially available scalpel blade. In this embodiment, the cutting edge 162 is linear.

Referring again to FIGS. 2-4, in addition to FIG. 8, the blade guide 104 retains the blade 160 generally in the medial-lateral and superior-inferior directions, but allows for sliding movement of the blade 160 within the guide 104 in substantially the anterior-posterior direction 113. Further detail regarding the blade guide 104 is provided below in connection with FIGS. 5 and 6.

The shoulder 168 of the blade frame 164 is configured to cooperate with the blade guide 104 to arrest a downward travel of the blade member 108 at a predetermined depth. The predetermined depth of travel distance of the blade member 108 corresponds to an incision by the blade 160 into the cricothyroid membrane when the frame 102 is disposed on a human with the protuberance 112 seated at least partly within the sternal notch 4 (see FIG. 1). The shoulder 168 is configured to interfere with the blade guide 104 such that the blade 160 punctures the cricothyroid membrane 2 but not the posterior tracheal cartilage.

Figure 7:
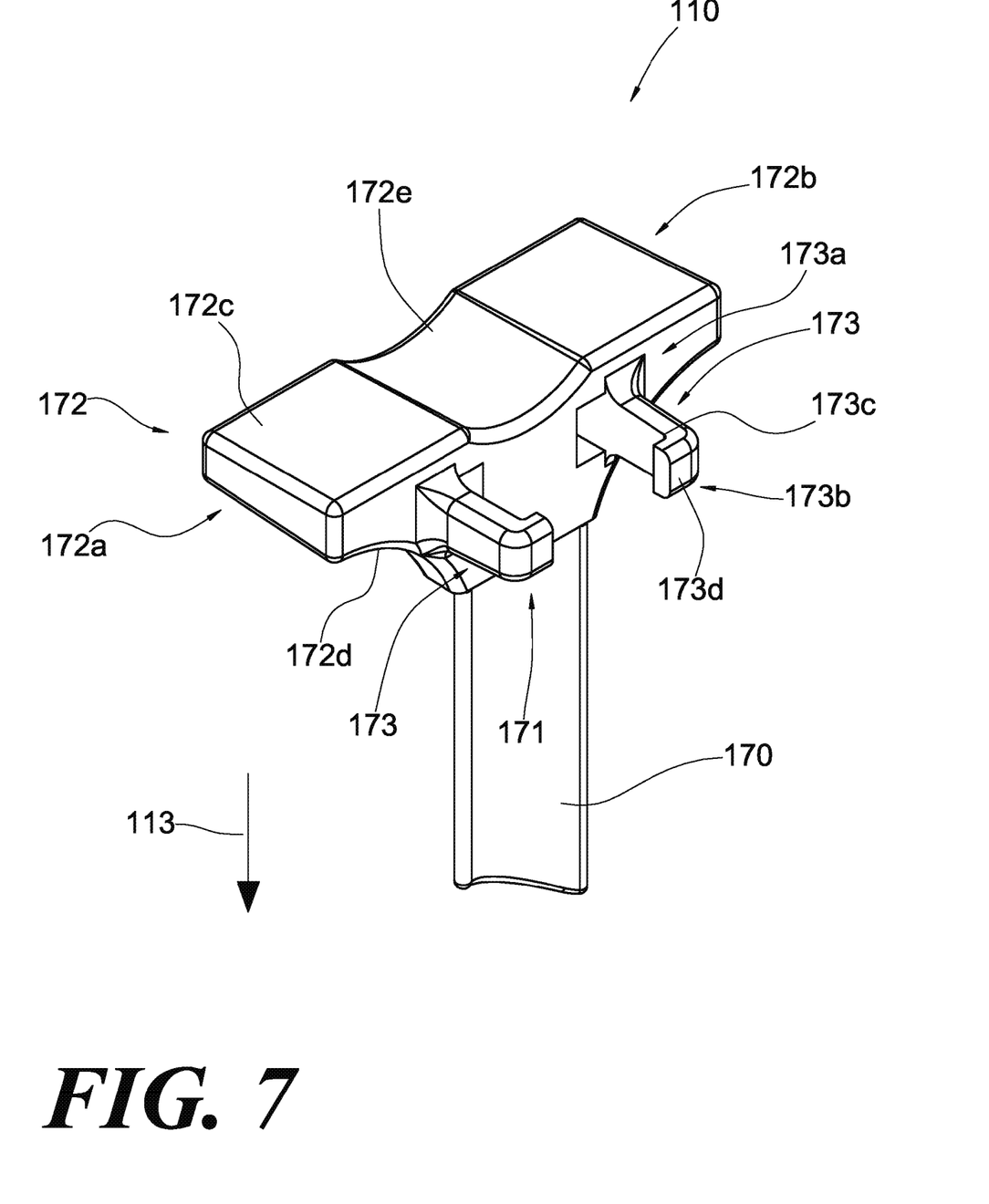
FIG. 7 shows a perspective view of an exemplary embodiment of the dilator of the cricothyrotomy apparatus of FIG. 2.

Referring to FIGS. 2, 3 and 7, the dilator 110 is a non-sharp, curved element that is preloaded into the dilator guide 106 of the frame 102 as shown in FIGS. 2 and 3. In general, the dilator 110 includes an elongate curved shaft 170 having a length comparable to that of the blade member 108, and a head portion 172 at one end. The dilator 110 may suitably be integrally formed of a rigid polymer. The dilator 110 is configured to be depressed (via the head portion 172) into the incision in the neck made by the blade member 108, either nearly at the same time as the incision, or after the blade edge 162 has passed into the neck. The dilator 110 is held inside the access hole in the tissue to maintain the hole before the breathing tube, not shown, is passed into the airway. The elongate curved member 170 of the dilator 110 acts as a backstop to direct the breathing tube into the airway.

In this embodiment, the head portion 172 of the dilator 110 includes a second blade guide 171 and first and second handle wings 172a, 172b. As will be discussed below, the second blade guide 171 is configured to retain the blade member 108 in the medial-lateral and superior-inferior directions, while allowing substantially linear movement of the blade member 108 relative to the dilator 110 in the anterior-posterior direction 113. As will also be discussed below, the first and second handle wings 172a, 172b form a handle and/or a push bar.

The second blade guide 171 in this embodiment includes first and second arms 173 extending out from a main body of the head portion 172, the arms 173 configured to retain the blade member in the medial-lateral and superior-inferior directions. Each arm 173 includes a bar 173c having a first end 173a affixed to the head portion 172, and extends to a second end 173b in the superior-inferior direction. Each arm 173 also includes a nub 173d extending from a second end 173b of the bar 173 along the anterior-posterior direction. It will be appreciated, however, that arms having other geometries may be used to constrain medial-lateral and superior-inferior movement of the blade member 108. Moreover, it will be appreciated that the second blade guide 171 in the alternative may comprise a closed loop, for example, where the arms 173 are connected by a bar extending from nub to nub.

The shaft 170 also includes a depression 170a on a rear side thereof, for receiving and engaging the clip 250 (see FIG. 3). In this embodiment, the depression 170a is formed as a linear channel similar to the depression 165c of the blade member 108. The depression 170a is aligned vertically with the depression 165c.

Referring again to the embodiment, of FIGS. 2, 3 and 7, the first and second handle wings 172a, 172b extend outward from a vertical axis of the elongate durved shaft 170. In general, the handle wings 172a, 172b provide exposed portions of the top surface 172c that may be manipulated to allow the blade member 108 to be separated from the dilator 110. The top surface 172c also defines a channel 172e receiving the correspondingly shaped portion of the button surface 166a of the blade member 108. Each of the first and second handle wings 172a, 172b have a lower surface 172d facing the anterior-posterior direction 113 that can be used as a finger pull.

Figure 9:
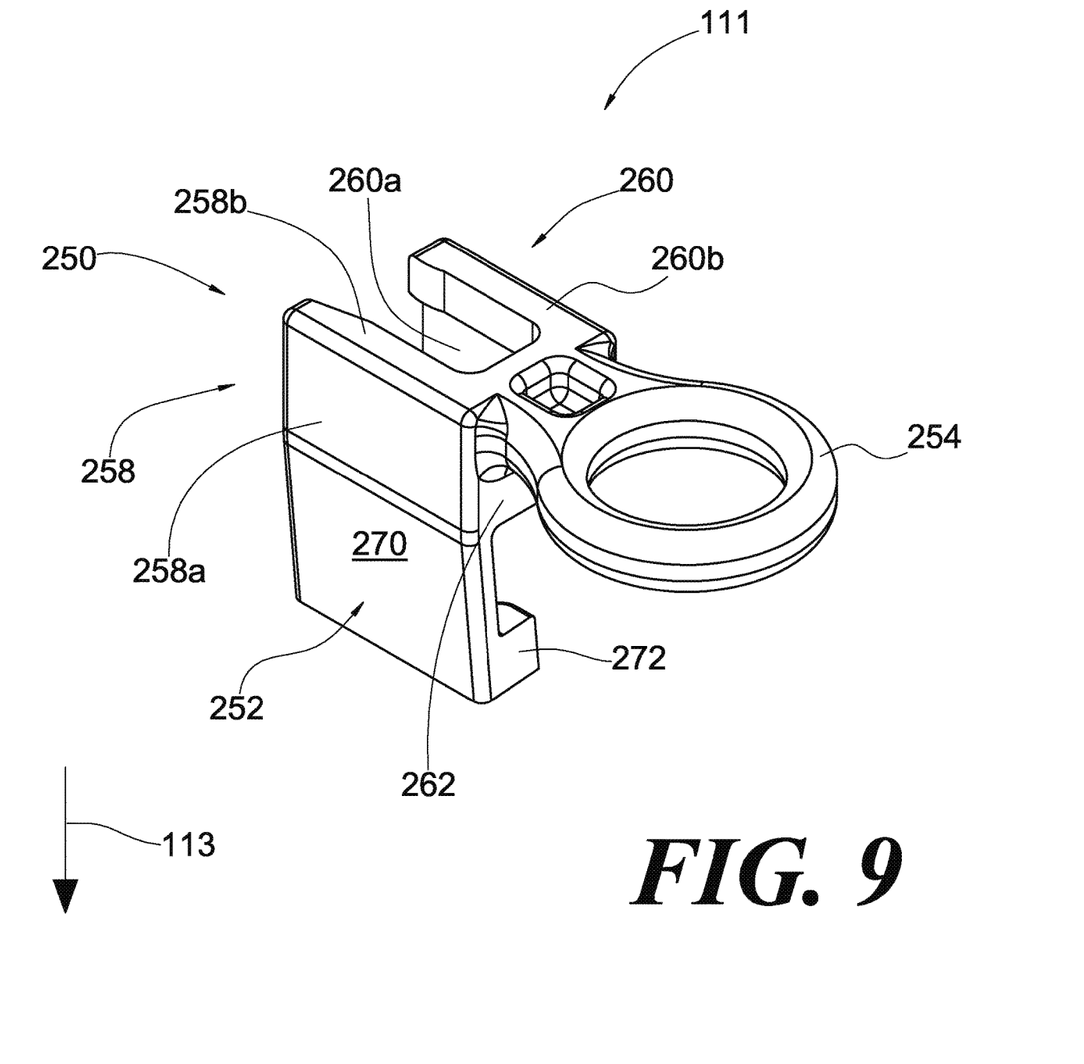
FIG. 9 shows a perspective view of an exemplary embodiment of the clip member of the cricothyrotomy apparatus of FIG. 2.

The clip member 111 of this embodiment is shown is described in reference to FIGS. 2, 3 and 9. The clip member 111 includes a clip 250, a shield 252, and a looped finger pull 254, integrally formed from molded plastic.

The clip 250 is a U-shaped member having opposing first and second clip arms 258 and 260 extending from a back plate 262. Each of the clip arms 258 and 260 includes a plate 258a, 260a and a jaw 258b, 260b. Each jaw 258b, 260b extends along the length of the plate 258a, 260a, and inward from each corresponding plate 258a, 260a toward the opposite plate 260a, 258a. Each jaw 258b, 260b has a shape corresponding to the depressions 165c and 170a. Each jaw 258b, 260b has a beveled inner surface at the end to facilitate placement over the depressions 265c and 170a.

The shield 252 includes a plate 270 that extends in the downward direction 113 from the removable clip 250, and specifically, the plate 258a of the clip arm 258. When the clip member 111 is installed (i.e. the jaws 258a, 258b are seated in the depressions 165c and 170a), the plate 270 extends adjacent to and covers at least the cutting edge 162 of the blade 160 to inhibit inadvertent access thereto, as is shown in FIG. 2, for example. The shield 252 further includes at least one nub 272 extending from the plate 270, such that when the clip member 111 is installed, the nub(s) 272 are adjacent to an underside of the blade guide 104 of the frame. The nubs 272 engage the frame to inhibit movement of the clip member 111, the blade member 108, and the dilator 110 vertically upward while the clip 111 is installed.

The finger loop 254 is configured to receive a human finger, and extends from the back plate 262 in a direction away from the clip arms 258, 260, or in other words, away from the open end of the clip 250. The finger loop 254 is used to provide leverage to remove the clip 250 from the installed position to allow the apparatus 100 to be used for the cricothyrotomy procedure.

Figure 5:
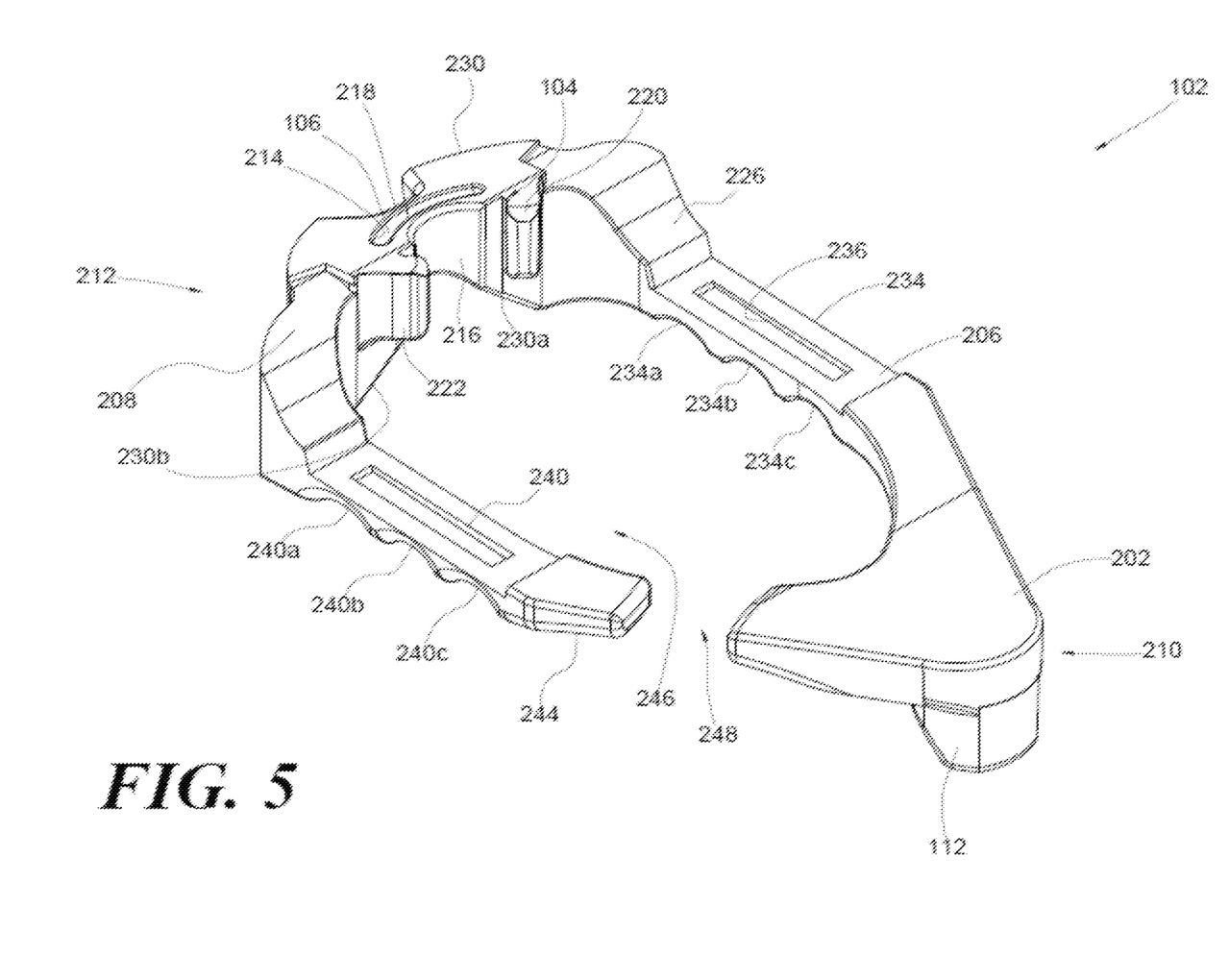
FIG. 5 shows a perspective view of exemplary frame of the cricothyrotomy apparatus of FIG. 2.
Figure 6:
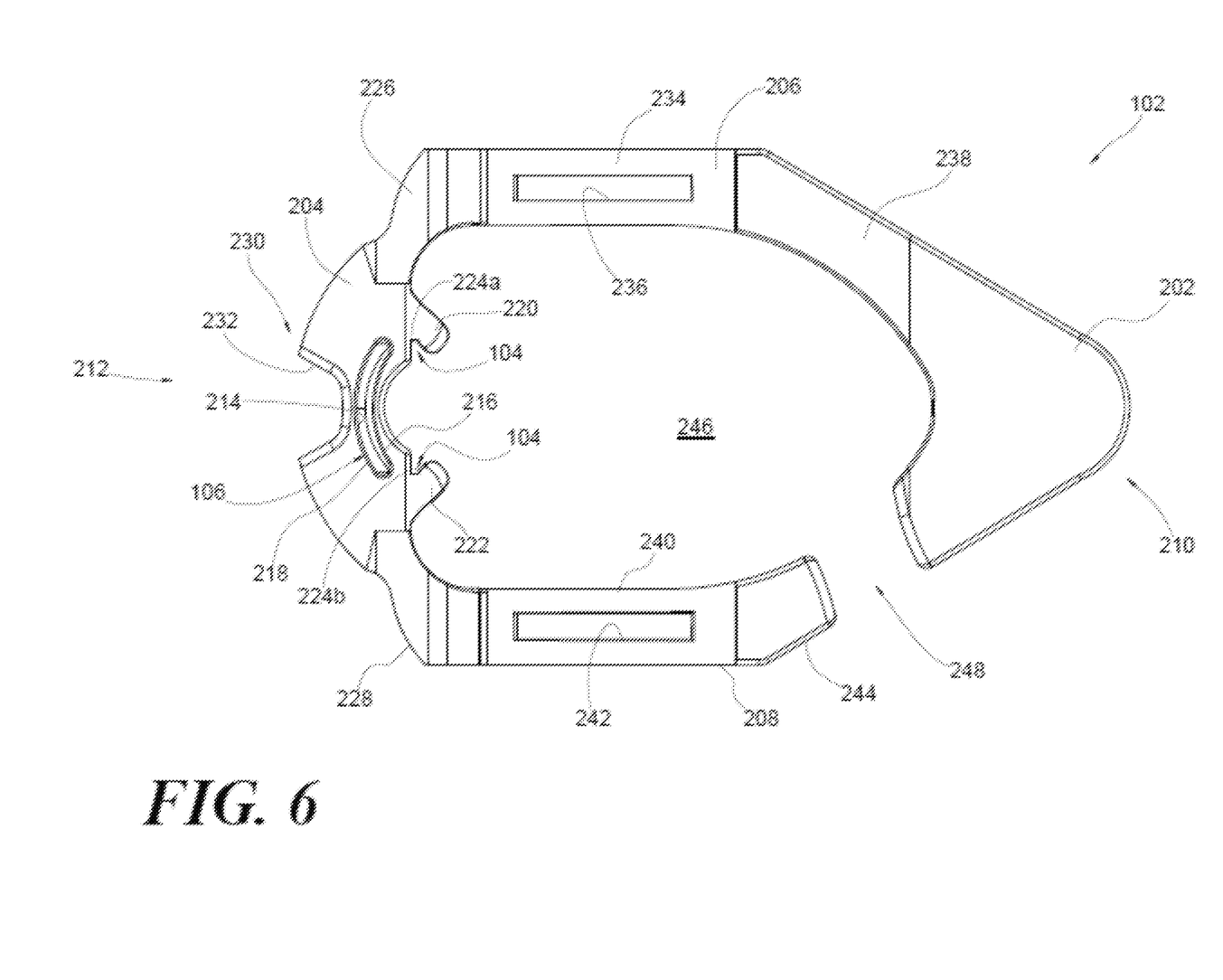
FIG. 6 shows a top plan view of the exemplary frame of FIG. 5.

FIG. 5 shows a perspective view of the frame 102 apart from the blade member 108, the dilator 110, and wings 126, 128 to provide additional clarity. FIG. 6 shows a plan view of the frame 102. With simultaneous reference to FIGS. 2, 5, and 6, the frame 102 includes a tail member 202, a jig 204, a first arm 206, a second arm 208. The tail member 202 is disposed at a first (inferior) end 210 of the frame 102, and the jig 204 is disposed at an opposing second (superior) end 212 of the frame 102. The protuberance 112 extends posteriorly from the tail member 202. The blade guide 104 and the dilator guide 106 are formed in the jig 204.

In particular, the jig 204 includes structural supports 226, 228 that extend medially, respectively, from the first arm 206 and second arm 208 to a central portion 230. The central portion 230 of the jig 204 includes the blade guide 104 and the dilator guide 106.

The dilator guide 106 is a sheath-like structure formed in the central portion of jig 204 having a curved channel 214 located medially on the jig 204. The channel 214 slightly concave toward the inferior direction, and forms a retaining channel for the elongate curved element 170 of the dilator 110, which is configured to slide in the anterior-posterior direction within the channel 214. (See FIG. 2). The channel 214 is largely formed by two spaced walls, an inferior wall 216 and a superior wall 218.

The central portion 230 of the jig 204 also includes two opposing notched extensions 220, 222 extending from the inferior wall 216. Each of the notched extensions 220, 222 define a corresponding notch 224a, 224b having open ends that face each other. The notches 224a and 224b collectively form the blade channel of the blade guide 104. The notched extensions 220, 222 cooperate with the blade shoulder 168 to limit the posterior travel of the blade 160. (See also FIGS. 3 and 8). The blade 160 otherwise slidably moves within the blade channel notches 224a, 224b when manipulated by the handle 166. The blade 160 is configured to seat within the channel notches 224a, 224b without sliding in the absence of applied pressure, using tension and/or stiction. To this end, the blade 160 may have a width that slightly exceeds that of the channel defined by the notches 224a, 224b.

The rear wall, or superior wall of the central portion 230 includes a medial notch 232 that allows for digital manipulation of the handle element 172 of the dilator 110 and blade handle 166. The bottom wall of the central portion 230 includes opposing inclined portions 230a, 230b and rounded concave intersection 230c therebetween. The portions 230a, 230b, and 230c collectively define a posterior facing curve in the bottom that can be used to help seat the frame 102 medial-laterally on the thyroid/neck. Thus, this curve 230a, 230b, and 230c, in combination with the protuberance 112, assist in proper placement of the apparatus 100 on the human neck.

The first arm 206 extends from the first end 210 of the frame 102 to the second end 212 of the frame 102. More specifically, the first arm 206 extends from the support element 226 of the jig 204 to the tail member 202. In this embodiment, the first arm 206 forms the structural member that connects, and thus defines the spacing between, the protuberance 112 on the tail member 202 and the blade guide 104 of the jig 204. The first arm 206 includes a straight beam 234 extending substantially in the inferior direction from the end of the support member 226. The straight beam 234 includes a central throughhole 236 which allows for the secure, overmolded, connection of the first wing 126. The underside of the straight beam 234 has a series of three concave depressions 234a, 234b, 234c. The first arm 206 also include a connector beam 238 that extends at an angle from the end of the straight beam 234 to the tail member 202. It will be appreciated that the throughhole 236 could be replaced by an indent that serves the same purpose.

In this embodiment, the second arm 208 forms the structural member that provides support, but does not connect the tail member 202 and the jig 204. The second arm 208 includes a straight beam 240 extending substantially in the inferior direction from the end of the support member 228. The straight beam 240 is substantially identical to the straight beam 234, and thus also includes a central throughhole 242 (or indent) which allows for the secure, overmolded, connection to the second wing 128. The underside of the straight beam 240 has its own series of three concave depressions 240a, 240b, 240c. The second arm 208 also includes a nub 244 of a connector beam that extends at an angle from the end of the straight beam 240, but stops short of the tail member 202.

The first arm 206 and second arm 208 thereby form a partial lateral enclosure around an open interior 246 of the frame 102. The discontinuity or void 248 formed between the nub 244 and the tail member 202 defines a passage through which a breathing tube, not shown, may pass out of the open interior 246 when the breathing tube is in place in the patient. This allows the apparatus 100 to be easily removed by lateral movement after the tube is inserted into the opening in the neck formed by the blade member 108 and dilator 110. Thus, the void 248 has a width that exceeds that of a breathing tube used for cricothyrotomies, the width of which would be known to those of ordinary skill in the art.

Referring again primarily to FIGS. 2 to 4, the wings 126, 128 are semi-rigid, slightly tacky wings or flaps configured to inhibit slippage of the apparatus 100 device during the procedure. The flexible wings 126, 128 are preferably formed by overmolding onto the more rigid frame 102. In this embodiment, the first wing 126 includes a two to four inch flap having rows and columns of protuberances or bumps 174 to aid in gripping strength. The second wing 128 has a substantially analogous structure.

In operation, the apparatus 100 is packaged for use such that the blade member 108 is preloaded in a blade guide 104 and the dilator 110 is preloaded in the dilator channel 106 as shown in FIGS. 2-4. To perform the procedure, the user first positions the preloaded apparatus 100 on the patient. To this end, the user aligns the frame 102 on the patient (see FIG. 1) using the protuberance 112, which seats in the sternal notch 4 of a patient. The user also seats the curve on the bottom wall of the central portion 230 on the trachea. The user then presses down on the wings 126, 128 to hold the frame 102 stable in position during the incision and tube insertion procedure. In position, the frame 102 seats along the midline of the neck across the trachea of a patient, such that all or part of the concave depressions 234a, 234b, 234c of the first arm 234 and the corresponding depressions 240a, 240b and 240c on the second arm 240 contact the skin. It will be appreciated that the open interior 246 allows for the neck to be visible and palpated while the apparatus 100 is held to the anatomy.

With the apparatus 100 in position (with the protuberance 112 seated at least in part in the sternal notch 12), the user first removes the clip member 111 by pulling on the finger loop 254. With the clip 250 removed from the depressions 170a, 165c, the nubs 272 and clip 250 no longer inhibit vertical movement of the blade member 108 and dilator 110.

The user then depresses the blade member 108 (via button 166) such that it travels posteriorly along the channel 224a, 224b of the blade guide 104, keeping the apparatus 100 aligned as the blade 160 is pressed into the tissue. The bottom surface 166a of the button 166 also causes the dilator 110 to travel downward or posteriorly. The travel of the blade member 108 stops at a predetermined depth when the shoulder 168 strikes the notched extensions 220, 222. It will be appreciated that interfering features of the blade member 108 and the blade guide 104 that stop the travel of the blade member 108 may take other suitable forms. In any event, the blade 160, shoulder 168 and blade guide 104 are configured such that the blade edge 162 does not perforate the posterior trachea. The blade 160 is designed to operate to a certain depth to allow cutting through overlying tissue anterior to the cricothyroid membrane and into the hollow cavity in the trachea.

The user then applies pressure to the exposed portions of the upper surface 172c of the handle wings 172a, 172b of the dilator 110. The user then lifts the button 166 to remove the blade 160 following the perforating procedure while pressing down on the upper surface 172c. Accordingly, the dilator 110 remains in place with the blade 160 removed to keep the airway open for placement of the breathing tube, or tracheal tube. Once the blade 160 is removed, the tracheal tube is placed into the patient's airway with the dilator 110 to guide the tube into the appropriate position in the patient's trachea. The user may then use the handle wings 172a, 172b to remove the dilator 110 from the patient's anatomy once the tube has been inserted into the trachea. Thereafter, the frame 102 may be moved away from the patient by laterally moving the frame 102 such that the in-place tube passes through the void 248.

The tube or breathing tube referred to herein may suitably be a 220 mm long polymer tube suitable for use for oral and nasal intubation and which has an inner diameter of 5.5 mm to 7.0 mm, and preferably 6.0 mm or 6.5 mm. The tube may also include an inflatable outer bag (and corresponding inflator) near the distal end which may be inflated to block the open airway interior that is exterior to the tube's outer diameter to ensure a direct pathway between the lungs and the exterior through the operative ends of the tube. Such tubes for use in cricothyrotomies are known to those of ordinary skill in the art. The tube in one embodiment also includes a throughhole in the side, between the distal end and the inflatable outer bag.

The cricothyrotomy apparatus and procedure discussed above may be used during emergency when other forms of establishing an airway are not possible or contraindicated. Such conditions may arise at a battlefield, in an ambulance, or at the site of the injury. One advantage of some embodiments is that the system provides a compact, low-cost, intuitive device that allows the user to make an accurate incision and quickly insert the tube into the patient's airway.

The frame 102 is preferably formed by injection molding of a hard polymer such as a polycarbonate ABS alloy. The wings 126, 128 are overmolded onto the frame 102 and are formed of a soft, tacky polymer such as a thermoplastic urethane. The blade member 108, the dilator 110, and the clip member 111 are separately formed using conventional techniques, such as molding. The blade member 108 and the dilator 110 are at least partially inserted into the frame 102 before use, with the clip member 111 in place, as shown in FIG. 2. As such, the apparatus 100 has a single piece construction that is ready to use.

It will be appreciated that the above-described embodiments are merely illustrative, and that those of ordinary skill in the art may readily define their own implementations and modifications that incorporate the principles of the present invention and fall within the spirit and scope thereof.

What is claimed is:

1. An incision and dilation apparatus for performing an incision in and dilating select tissue of a mammal, comprising:
    a blade member including a blade having a cutting edge;
    a dilator configured to dilate the select tissue;
    a frame including a blade guide, the frame adapted to position the blade guide over the select tissue, the blade guide configured to retain the blade member in first and second perpendicular directions and allow substantially linear movement of the blade member in a third direction, the frame further supporting the dilator and allowing movement of the dilator in the third direction;
    wherein the dilator includes a second blade guide configured to retain the blade member in first and second perpendicular directions and allow substantially linear movement of the blade member relative to the dilator in a third direction.

2. The incision and dilation apparatus of claim 1 wherein the blade member further comprises a blade frame, wherein the blade is supported by the blade frame and extends from a first end of the blade frame such that a blade edge of the is external to the blade frame.

3. The incision and dilation apparatus of claim 2, wherein the blade frame includes a sliding bar extending in the third direction, and a button disposed at a second end of the blade frame and extending in a direction other than the third direction, the button configured to engage a top surface of the dilator.

4. The incision and dilation apparatus of claim 3, wherein the cutting edge is linear.

5. The incision and dilation apparatus of claim 3, wherein the sliding bar includes a shoulder, the shoulder configured to engage the blade guide of the frame to limit the movement of the blade member in the third direction.

6. The incision and dilation apparatus of claim 3, wherein the dilator includes a dilation shaft that extends in the third direction, and head portion at one end of the dilation shaft, the head portion include the top surface of the dilator.

7. The incision and dilation apparatus of claim 6, wherein the dilation shaft has a curved cross-section.

8. The incision and dilation apparatus of claim 7, wherein the head portion of the dilator includes first and second wings extending outward from an axis of the shaft, the first and second wings each having a surface facing the third direction configured to be used as a finger pull.

9. The incision and dilation apparatus of claim 7, wherein the top surface of the head portion defines a channel receiving a correspondingly shaped portion of the button of the blade member.

10. The incision and dilation apparatus of claim 1, wherein the second blade guide includes first and second arms configured to retain the blade member in first and second perpendicular directions.

11. The incision and dilation apparatus of claim 10, wherein each of the first and second arms includes a bar extending from a first end in a first direction from another portion of the dilator, and further includes a nub extending from a second end of the bar along the second direction.

12. The incision and dilation apparatus of claim 1, further comprising a removable clip extending over and engaging a portion the dilator and the blade member to restrict movement of at least the blade member.

13. An incision and dilation apparatus for performing an incision in and dilating select tissue of a mammal, comprising:
    a blade member including a blade;
    a dilator configured to dilate the select tissue;
    a frame including a blade guide, the frame adapted to position the blade guide over the select tissue, the blade guide configured to retain the blade member in first and second perpendicular directions and allow substantially linear movement of the blade member in a third direction, the frame further supporting the dilator and allowing movement of the dilator in the third direction; and
    a removable clip extending over and engaging a portion the dilator and the blade member to restrict movement of at least the blade member.

14. The incision and dilation apparatus of claim 13 wherein the blade member further comprises a blade frame and the blade having a cutting edge, the blade supported by the blade frame and extending from a first end of the blade frame such that a blade edge of the is external to the blade frame, the blade frame having a sliding bar containing at least a portion of the blade, the sliding bar including a depression; and wherein the clip engages the depression of the sliding bar to engage the blade member.

15. The incision and dilation apparatus of claim 14, wherein the dilator further includes a dilator shaft, the dilator shaft including a depression, and wherein the clip further engages the depression in the dilator shaft.

16. The incision and dilation apparatus of claim 15, further comprising a shield formed with and extending in the third direction from the removable clip, the shield including a plate extending adjacent to the cutting edge to inhibit inadvertent access to the cutting edge.

17. The incision and dilation apparatus of claim 16, further comprising at least a portion of a loop formed with and extending opposite an open end of the clip, the at least portion of the loop configured to receive a human finger.

18. The incision and dilation apparatus of claim 13, further comprising a shield formed with and extending in a first direction from the removable clip, the shield including a plate extending adjacent to the cutting edge to inhibit inadvertent access to the cutting edge.

19. The incision and dilation apparatus of claim 17, wherein the shield further includes at least a first nub extending from the plate and adjacent to an underside of the blade guide of the frame.

20. The incision and dilation apparatus of claim 13, further comprising at least a portion of a loop formed with and extending opposite an open end of the clip, the at least portion of the loop configured to receive a human finger.

* * * * *